United States Patent [19]
Kelley et al.

[11] Patent Number: 5,610,065
[45] Date of Patent: Mar. 11, 1997

[54] INTEGRATED CHEMICAL/BIOLOGICAL TREATMENT OF ORGANIC WASTE

[75] Inventors: Robert L. Kelley, Mt. Prospect; Andy H. Hill, Glen Ellyn; Vipul J. Srivastava, Forest Park; W. Kennedy Gauger, Pflugerville; John J. Kilbane, II, Woodstock, all of Ill.

[73] Assignee: Institute of Gas Technology, Chicago, Ill.

[21] Appl. No.: 402,421

[22] Filed: Mar. 10, 1995

Related U.S. Application Data

[63] Continuation-in-part of Ser. No. 56,527, May 3, 1993, abandoned, which is a continuation-in-part of Ser. No. 718,330, Jun. 21, 1991, abandoned.

[51] Int. Cl.$^6$ ................................................. C12S 3/02
[52] U.S. Cl. ........................ 435/264; 435/262; 435/262.5
[58] Field of Search ................................ 435/264, 262, 435/262.5

[56] References Cited

U.S. PATENT DOCUMENTS

| | | |
|---|---|---|
| 4,234,689 | 11/1980 | Gutnick et al. . |
| 4,321,143 | 3/1982 | Wilms et al. . |
| 4,370,241 | 1/1983 | Junkermann et al. . |
| 4,387,018 | 6/1983 | Cook et al. . |
| 4,447,541 | 5/1984 | Peterson . |
| 4,604,214 | 8/1986 | Carr et al. . |
| 4,724,084 | 2/1988 | Pahmeier et al. . |
| 4,804,480 | 2/1989 | Jayawant . |
| 4,954,258 | 9/1990 | Little ....................................... 435/264 |
| 5,334,533 | 8/1994 | Culasitu et al. ........................ 435/264 |

FOREIGN PATENT DOCUMENTS

| | | |
|---|---|---|
| 2533775 | 3/1977 | Germany . |

OTHER PUBLICATIONS

Bedard, D. L. et al., *Applied and Environmental Microbiology*, 51(4), pp. 761–768, Apr. 1986.

Kensuke Furukawa, "Microbial Degradation of Polychlorinated Biphenyls (PCBs)," Biodegradation and Defoxification of Environmental Pollutants, Chapter 2, pp. 33–57.

D. Kamely, A. Chakrabarty, and G. S. Omenn, "Bacterial Transformation of Polychlorinated Biphenyls," Biotechnology and Biodegradation, vol. 4, 1990, pp. 369–388.

Michael P. Shiars, "Seasonal Biotransformation of Naphthalene, Phenanthrene, and Benzo[a]pyrene in Surficial Estuarine Sediments," Applied and Environmental Microbiology, Jun. 1989, pp. 1391–1399.

Susan C. Wilson & Kevin C. Jones, "Bioremediation of Soil Contaminated with Polynuclear Aromatic Hydrocarbons (PAHs): A Review," Environmental Pollution, vol. 81, 1993, pp. 229–249.

Kap S. Park et al., "Fate of PAH Compounds in Two Soil Types: Influence of Volatilization, Abiotic Loss and Biological Activity," Environmental Toxicology and Chemistry, vol. 9, 1990, pp. 187–195.

(List continued on next page.)

*Primary Examiner*—Helen Pratt
*Attorney, Agent, or Firm*—Speckman, Pauley & Fejer

[57] ABSTRACT

A process for improved remediation of polynuclear aromatic hydrocarbon and/or polychlorinated hydrocarbon contaminated solid materials by integrated chemical/biological treatment comprising contacting the polynuclear aromatic hydrocarbon and/or polychlorinated hydrocarbon for chemical treatment with hydrogen peroxide in the presence of ferrous ion in liquid solution at a temperature of about 10° C. to about 100° C., oxidizing the polynuclear aromatic hydrocarbon materials and/or polychlorinated hydrocarbon materials and producing more readily biodegradable hydrocarbon product materials, and then biodigesting the product materials by aerobic and/or anaerobic biodigestion. A lower alcohol added to the chemical treatment in accordance with one embodiment further enhances oxidation of 4- to 6-ring aromatic hydrocarbon contaminants.

27 Claims, 4 Drawing Sheets

OTHER PUBLICATIONS

ATCC, Catalogue of Bacteria & Bacteriophages, American Type Culture Collection, 17th Edition, 1989, pp. 14, 166, and 263.

ATCC, Catalogue of Fungi/Yeasts, American Type Culture Collection, 16th Edition, 1984, p. 267.

Eric C. Yost, Dale W. Finnesgaard, and Lawrence D. Dalen, "Bioremediation of Contaminated Soil From Wood Treating Wastes," Gas, Oil, and Environmental Biotechnology VI, edited by Vipul Srivastava and Jared Smith, Institute of Gas Technology, and Thomas D. Hayes, Gas Research Institute, Institute of Gas Technology, Des Plaines, Illinois, pp. 371–399.

Richard J. Bigda, The Technotreat Corp., "Fenton's Chemistry: An Effective Advanced Oxidation Process," Environmental Technology, May/Jun. 1996, pp. 34–39.

Blanca S. Hernandez, Joseph J. Arensdorf & Dennis D. Focht, "Catabolic Characteristics of Biphenyl–Utilizing Isolates Which Cometabolize PCBs," Bidegradation 6:75–82, 1995, pp. 75–82.

Daniel A. Abramowicz, "Aerobic and Anaerobic Biodegradation of PCBs–A Review," Biotechnology, 1990, pp. 241–251.

Vipul J. Srivastava, John J. Kilbane, Robert L. Kelley, Cavit Akin, Thomas D. Hayes, and David G. Linz, "Biodegradation of Old Town Gas Site Waste," IGT Symposium on Gas, Oil, and Coal Biotechnology, New Orleans, Louisiana, Dec. 5–7, 1988.

W. Kennedy Gauger and Vipul J. Srivastava, "Bioremediation of Gas Industry Wastes: Current Status and New Directions," Hazardous Waste and Environmental Management in the Gas Industry Symposium, Chicago, Illinois, Jun. 13, 1990.

"Catalogue of Bacteria and Phages", American Type Culture Collection, 17th Edition, 1989.

Mueller J. G. et al., "Isolation and Characterization of a Fluoranthene–Utilizing Strain of *Pseudomonas paucomibilis*" Applied Environmental Microbiology, 56:1079–1086 (1990).

Mueller J. G. et al., "Action of Fluoranthene–Utilizing Bacterial Community on Polycyclic Aromatic Hyrocarbon Components of Creosote,"Applied Environmental Microbiology, 55:3085–3090 (1989).

INTEGRATED CHEMICAL/BIOLOGICAL TREATMENT OF ORGANIC WASTE

CROSS REFERENCE TO RELATED APPLICATIONS

This application is a continuation-in-part application of our application having Ser. No. 08/056,527 now abandoned, filed May 3, 1993,which application is a continuation-in-part application of our previously filed application having Ser. No. 07/718,330, filed Jun. 21, 1991, now abandoned.

BACKGROUND OF THE INVENTION

1. Field of the Invention

This invention relates to integrated chemical/biological treatment providing improved remediation of undesired organic solid components in materials such as soils, sediments, sludges and slurries containing such solid organopollutants, particularly polynuclear aromatic hydrocarbons and polychlorinated hydrocarbons. The process generally involves chemical oxidation or partial oxidation with hydrogen peroxide in the presence of ferrous ion, such as Fenton's Reagent ($H_2O_2/Fe^{++}$), under specified conditions followed by aerobic and/or anaerobic microbial digestion.

2. Description of Related Art

A number of prior references teach treatment of organic-containing effluents with hydrogen peroxide and iron. U.S. Pat. No. 4,321,143 teaches decreasing COD-content of effluent by treating with hydrogen peroxide in the presence of a transition metal compound, for decomposition of the hydrogen peroxide, by adjusting the pH of the effluent to about 4 to 5, adding about 55 to 63% of the calculated quantity of $H_2O_2$ required for the total oxidation of the total COD-content, dissolving an iron compound in the effluent so that the molar ratio of $H_2O_2$ to iron is about 20:1 to 10:1, maintaining the temperature at about 5° to about 100° C., adding a base to adjust the pH to about neutral, separating flocculated material, and subjecting the effluent to biological degradation.

Oxidation of certain aromatic chemicals using Fenton's Reagent is known: U.S. Pat. No. 4,604,214 teaches removal of nitrocresols from dinitrotoluene waste water streams by adjustment of pH to below about 4 with an aqueous acid followed by contact with Fenton's Reagent, about 1.1 to 3.0 weight ratio of peroxide to total nitrocresols and ferrous salt to provide $2.5-5\times10^{-3}M$, at 70° to 90° C. for about one half to one hour; U.S. Pat. No. 4,804,480 teaches destroying polynitrophenols or their salts in an aqueous waste by treating with at least two moles of hydrogen peroxide per mole of nitrophenol in the presence of from 0.002 to 0.7 moles of an iron salt per mole of polynitrophenol and at a pH lower than 4 and a temperature greater than 65° C.; U.S. Pat. No. 4,370,241 teaches treatment of waste water containing phenol or a phenol derivative with hydrogen peroxide in the presence of metallic iron or copper with a specified activator which is a salt of an alkali metal, alkaline earth metal, zinc, aluminum, nickel, manganese or insoluble silica, the activator being present in an amount of 0.1 to 0.2 percent based upon the hydrogen peroxide and the treatment is said to be independent of pH. U.S. Pat. No. 4,724,084 teaches removal of toxic organics and heavy metals from waste water discharged from airplane manufacturing processes by using ferrous sulfate catalyzed hydrogen peroxide at an initial pH of about 5 for oxidation of phenol followed by flocculation of metals and repeating the oxidation step with ferrous sulfate catalyzed hydrogen peroxide.

Soil decontamination by desorption and dehalogenation of polyhalogenated contaminants is taught by U.S. Pat. No. 4,447,541 to be effected by an alkaline constituent of an alkali metal hydroxide and a monohydric or dihydric alcohol together with a sulfoxide catalyst followed by biological degradation of the more highly biodegradable hydrolyzed organics. U.S. Pat. No. 4,387,018 teaches removal of polychlorinated biphenyl from oil by extracting the biphenyls into methanol and separation by distillation.

The publication "Biodegradation of Old Town Gas Site Wastes," Vipul J Srivastava, John J. Kilbane, Robert . L. Kelley, Cavit Akin, Thomas D. Hayes and David G. Linz, *IGT Symposium on Gas, Oil., and Coal Biotechnology*, New Orleans, La., Dec. 5–7, 1988 generally suggests treatment of pyrene and thianthrene with hydrogen peroxide and ferrous sulfate for oxidizing polynuclear aromatic hydrocarbons to complement in-situ biological treatment processes.

A current review of bioremediation of liquid and solid organic contaminated wastes points out many problems, particularly in the bioremediation of solids contaminated with aromatic hydrocarbons, most particularly the polynuclear aromatic hydrocarbon contaminants having about 4 to about 6 rings, is described in "Bioremediation of Gas Industry Wastes: Current Status and New Directions," W. Kennedy Gauger and Vipul J. Srivastava, *Hazardous Waste and Environmental Management in the Gas Industry Symposium*, Chicago, Ill., Jun. 13, 1990.

SUMMARY OF THE INVENTION

There is the need for a process which highly oxidizes contaminant complex polynuclear aromatic hydrocarbons, particularly those having about 4 to about 6 carbon rings, and polychlorinated hydrocarbons, in high concentrations of solids, such as in liquid slurries, to provide product materials which are more amenable to biological degradation.

It is an object of this invention to provide a process for high degree chemical oxidation of polynuclear aromatic hydrocarbons and/or polychlorinated hydrocarbons using hydrogen peroxide in the presence of ferrous ion followed by biological degradation to obtain high remediation of polynuclear aromatic hydrocarbon and/or polychlorinated hydrocarbon contaminated solids.

It is another object of this invention to provide an integrated chemical/biological treatment process for remediation of higher polynuclear aromatic hydrocarbon and/or polychlorinated hydrocarbon contaminated solid waste materials in which high concentrations of solids can be chemically oxidized at about ambient temperatures.

It is yet another object of this invention to provide an integrated chemical/biological treatment process for polynuclear aromatic hydrocarbon and/or polychlorinated hydrocarbon contaminated solid waste materials which is enhanced by the presence of methanol and/or ethanol during chemical treatment with hydrogen peroxide in the presence of ferrous ion.

These and other objects and advantages of the integrated chemical/biological treatment process according to this invention may be achieved by chemical treatment of undesired polynuclear aromatic hydrocarbon and/or polychlorinated hydrocarbon contaminated solid materials by contact with hydrogen peroxide in the presence of ferrous ion, preferably in a liquid solution, forming a mixture, or slurry, at a temperature of about 10° C. to about 100° C. oxidizing the polynuclear aromatic hydrocarbons and/or polychlorinated hydrocarbons, thus producing more readily biodegradable hydrocarbon product materials, and then biodigesting such product materials by at least one of aerobic and/or anaerobic biodigestion. The process may be even further enhanced by increased total oxidation of the polynuclear aromatic hydrocarbons and/or polychlorinated hydrocarbons to carbon dioxide by the presence of a lower alcohol in the hydrogen peroxide containing slurry. The process of this invention is extremely flexible, providing combinations of biological treatments and various manners of recycle. The integrated chemical/biological treatment process according to this invention may also be performed on solids in-situ, such as in-situ contaminated soils.

It is known that hydroxylation of organic compounds is a necessary step for biological degradation and increases the solubility of polynuclear aromatic hydrocarbons. It is also known that Fenton's reaction hydroxylates organic compounds. As a result, it is apparent that chemical treatment of the polynuclear aromatic hydrocarbons in accordance with the integrated process of this invention increases the biodegradability and bioavailability of the polynuclear aromatic hydrocarbons. Experiments which we have conducted show that more polar intermediates are also formed to provide enhanced biodegradability. In addition, the chemical treatment in accordance with the process of this invention modifies the texture of the soil in which the polynuclear aromatic hydrocarbons are disposed as well as the interaction between the sorbed organopollutant and the soil matrix, making the organopollutant more available for desorption and biodegradation. Although biosurfactants are known to be effective on lower molecular weight organic compounds, they have not been shown to be effective on higher molecular weight compounds, such as 4- to 6-ring polynuclear aromatic hydrocarbons. Mueller J. G. et al., "Isolation and Characterization of a Fluoranthane-Utilizing Strain of *Pseudomonas paucimobilis,*" *Applied Environments Microbiology,* 56:1079–1086 (1990) and Mueller, J. G. et al., "Action of Fluoranthene-Utilizing Bacterial Community on Polycyclic Aromatic Hydrocarbon Components of Creosote," *Applied Environmental Microbiology,* 55:3085–3090 (1989) describe the enhanced biodegradability of fluoranthene and other polynuclear aromatic hydrocarbons by the addition of 200 ppm Tween 80, a known surfactant, albeit not a biosurfactant.

It will also be apparent to those skilled in the art that the non-specific nature of the Fenton's reaction requires enough hydrogen peroxide to degrade all organics. In direct contrast thereto, we have found that the polynuclear aromatic hydrocarbons sorbed to the soil matrices are selectively degraded and that, as a result, good results are obtained using less hydrogen peroxide.

BRIEF DESCRIPTION OF THE DRAWING

The invention will be more fully understood by description of preferred embodiments in conjunction with the drawings wherein.

DESCRIPTION OF PREFERRED EMBODIMENTS

Figure 1:
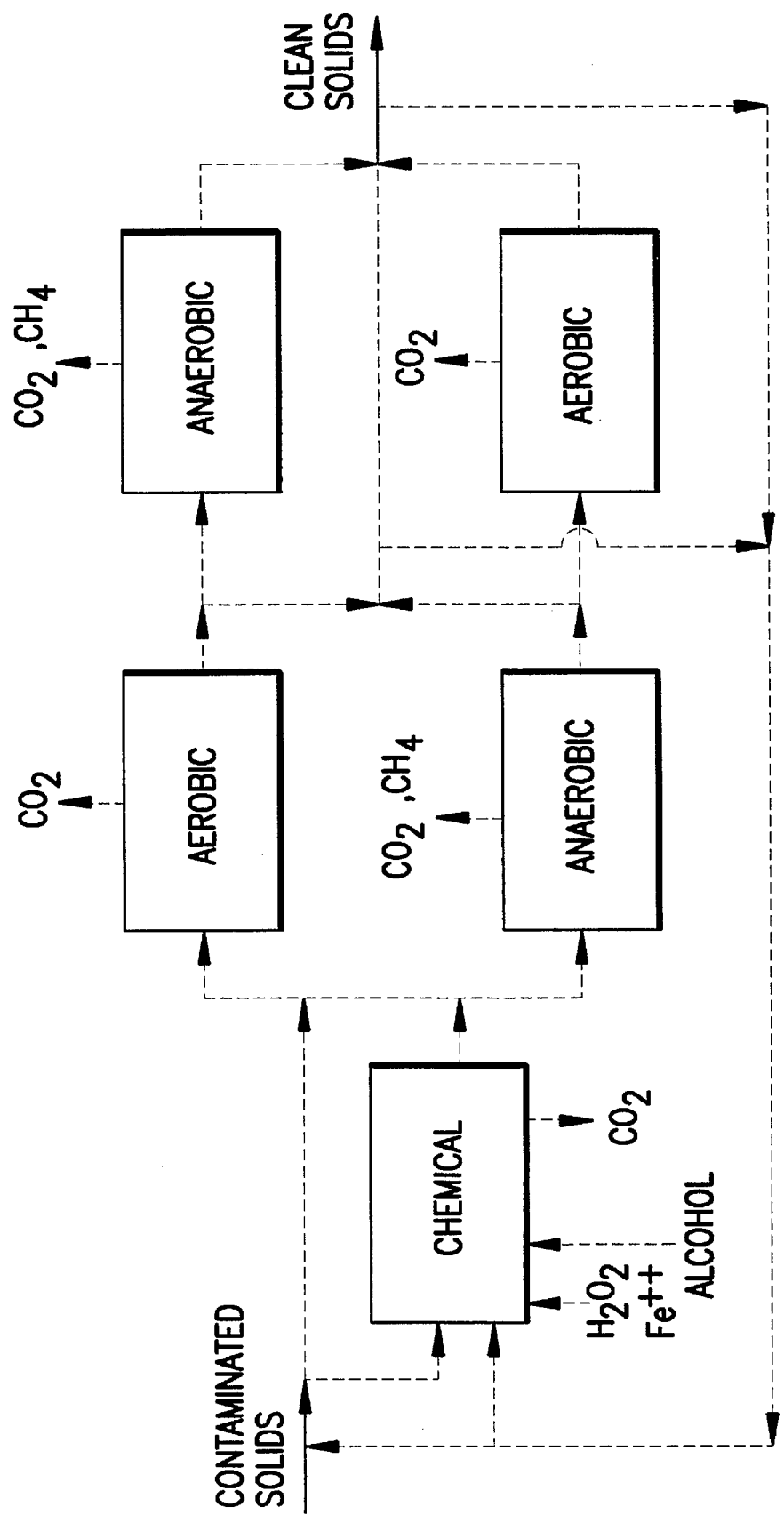
FIG. 1 very schematically shows in dashed lines various alternative routes for the flow of various embodiments of this invention.

Town gas or manufactured gas plants have contaminated soils with wastes of organic polynuclear aromatic hydrocarbon fused-ring compounds, the higher numbered ring compounds, particularly those having about 4 to about 6 rings, being generally recalcitrant to bioremediation. This recalcitrance is magnified when the contaminant is associated with a solid material, such as soil, and when the organic waste content is high, such as over 5,000 to 10,000 ppm and up to 30,000 to 40,000 ppm, as is the case with many organic polynuclear aromatic hydrocarbon contaminated soils. Solvent extraction of the organic contaminant has been performed to provide a liquid bioremediation system which is known to be more effective than a solid treatment system, but in many instances, the extracting liquids were not compatible with the microorganisms, and the desired uniformity of degradation, particularly of 4- to 6-ring aromatic compounds, could not be obtained.

When referring to 4- to 6-ring polynuclear aromatic hydrocarbon compounds, we mean to include compounds such as pyrene, fluoranthene, chrysene, benz(a)anthracene, benzo(a)pyrene, benzo(e)pyrene, benzo(b)fluoranthene, benzo(k) fluoranthene, benzo(g,h,i)perylene, indeno(1,2,3-cd)pyrene, dibenzo(a,h)anthracene, and their substituted derivatives. We have found that the hydrogen peroxide chemical oxidation combined with biodigestion according to the present invention preferentially destroys the 4- to 6-fused-ring polynuclear aromatic compounds, as compared to the 2- to 3-fused-ring polynuclear aromatic compounds. The synergism of the integrated chemical/biological treatment process according to the present invention with respect to the 4- to 6-fused-ring polynuclear aromatic hydrocarbon compounds is even further amplified by the concurrent chemical treatment of the contaminated solids with hydrogen peroxide in the presence of a lower alcohol, such as methanol or ethanol. This is especially unexpected because the addition of any organic compound would be expected to quench the oxidation of the polynuclear aromatic hydrocarbon compounds by the hydrogen peroxide, while in this case it significantly increases the oxidation, particularly of 4- to 6-ring polynuclear aromatic hydrocarbon compounds. It is known that the prior addition of organic materials is detrimental; for example, prior composting with cattle manure significantly decreases the desired oxidation effect of hydrogen peroxide because the active hydroxyl ions are apparently consumed by active organic materials other than the polynuclear aromatic hydrocarbon compounds. The lower molecular weight alcohols are thought to increase the aqueous solubility of polynuclear aromatic hydrocarbons, in particular 4- to 6-ring polynuclear aromatic hydrocarbons, thereby rendering them more susceptible to oxidation by Fenton's reaction.

The synergism of the integrated chemical/biological treatment in accordance with the process of this invention is demonstrated in the following Table I which shows the results of separate chemical treatment and biological treatment on a variety of polynuclear aromatic hydrocarbons compared to the results derived from treatment of the polynuclear aromatic hydrocarbons in accordance with the integrated chemical/biological treatment of the process of this invention. The results show increased reduction in the concentration of polynuclear aromatic hydrocarbons in contaminated soils treated in accordance with the integrated chemical/biological process of this invention compared to the results derived from treatment of the contaminated soils by separate chemical treatment and biological treatment.

TABLE I

|  | $C_i^1$, ppm | $C_f^2$, ppm (% reduction[3]) | | |
| --- | --- | --- | --- | --- |
|  |  | $C^4$ | $B^5$ | $CB^6$ |
| Naphthalene | 92 | 87 (5) | 63 (32) | 26 (71) |
| 2-Fluorobiphenyl | 200 | 199 (1) | 200 (0) | 196 (2) |
| Acenaphthylene | 236 | 203 (14) | 120 (49) | 52 (78) |
| Acenaphthene | 37 | 37 (0) | 7 (81) | 3 (92) |
| Fluorene | 330 | 316 (4) | 50 (85) | 22 (93) |
| Phenanthrene | 934 | 932 (0) | 209 (78) | 87 (91) |
| Anthracene | 360 | 361 (0) | 144 (60) | 56 (84) |
| Fluoranthene | 581 | 584 (0) | 572 (2) | 283 (51) |
| Pyrene | 437 | 429 (2) | 510 (0) | 288 (34) |
| Benz(a)anthracene | 265 | 269 (0) | 484 (0) | 247 (7) |
| Chrysene | 217 | 222 (0) | 419 (0) | 214 (1) |
| Benzo(b)fluoranthene | 140 | 138 (1) | 312 (0) | 139 (1) |
| Benzo(a)pyrene | 188 | 195 (0) | 436 (0) | 182 (3) |

[1]Initial concentration of PAH before treatment.
[2]Final concentration of PAH after each treatment.
[3]$100 \ast (C_i - C_f) / C_i$
[4]Chemical treatment by Fenton's chemical oxidation. (Soil slurry was chemically treated at day 0 and result was monitored at day 2.)
[5]Biological treatment by supplying nutrient media to soil slurry. (Result was monitored after 50 day treatment.)
[6]Chemical treatment combined with biological treatment - Fenton's chemical oxidation followed by microbes inoculation. (Soil slurry was chemically oxidized at day 0 and 38, followed by inoculation of microbes at day 3 and 41, respectively. Result was analyzed at day 50.)

The integrated chemical/biological treatment according to this invention may be carried out using any solid material contaminated with undesired polynuclear aromatic hydrocarbon compounds, particularly those having about 4 to about 6 fused-rings which are recalcitrant to biodegradation and/or polychlorinated hydrocarbon compounds. The treatment according to this invention may be applied to solids, such as soils, sands, clay and humic material present in soils and sludges, prior to initial biodigestion which is preferable when the solids contain a relatively high amount of 4- to 6-ring compounds, or the treatment according to this invention may be applied to solids, such as biodigester sludges, following initial biodigestion which is preferable when the untreated solids originally contained a relatively high amount of readily biodigestible 2- to 3-ring compounds in the total polynuclear aromatic hydrocarbon compound contamination. Thus the chemical portion of the treatment according to the present invention may be applied to the raw soil solids prior to biodigestion or may be applied to digester effluent solids for recycle or passage to a different type of biodigestion. FIG. 1, in simplified schematic manner, shows by dashed lines various alternative manners in which solids may be remediated in accordance with the process of this invention in which chemical oxidation by hydrogen peroxide in the presence of ferrous ion is followed by biodigestion of the treated solids. The contaminated solids may be first subjected to chemical treatment followed by at least one of or both aerobic and/or anaerobic digestion in either order and the digester solids removed as clean solids or recycled to chemical treatment and further bioremediation, or the contaminated solids may be first subjected to biological treatment by at least one or both aerobic and/or anaerobic digestion in either order and the digester solids passed to chemical treatment following which the chemically treated solids are recycled to at least one or both aerobic and/or anaerobic digestion and again recycled or withdrawn as clean solids. Treated solids may be further treated by either or both the chemical and/or biodigestion portion of the process of this invention any number of times to obtain the desired removal of polynuclear aromatic hydrocarbon compounds.

Both aerobic and anaerobic biodigestion are suitable for use individually or in combination in the biological portion of the treatment process of this invention, dependent upon contaminants which may be dominant in the solids. For example, when the predominant contaminants are trichloroethylene or polynuclear aromatic hydrocarbons, the preferred choice would be aerobic digestion followed by anaerobic digestion while, when the predominant contaminants are materials such as polychlorinated biphenyls, the preferred sequence would be anaerobic digestion followed by aerobic digestion. Suitable aerobic and anaerobic digestion media are known to the art. For example, digestion media suitable for biodigestion of polynuclear aromatic hydrocarbons include basic mineral salt media (BMS) with sufficient nitrogen, sulfur and phosphorous to support microbial growth. Suitable microorganisms for biodigestion comprise *Pseudomonas aeruginosa* (ATCC 15522-28, 21472), *Alcaligenes faecalis* (ATCC 8750), *Rhodotorula rubra* (ATCC 16639), and *Xanthomonas maltophilia* (ATCC 25556).

The process according to the present invention is carried out by contacting for chemical treatment polynuclear aromatic hydrocarbon contaminated solid material with a liquid solution, preferably aqueous, forming a mixture containing at least sufficient, and preferably an excess of, ferrous ion to enable complete reaction with the total added hydrogen peroxide to form the desired hydroxyl radical oxidant. We have found amounts, based upon the total mixture being treated, of about 0.1 weight percent to about 10 weight percent total hydrogen peroxide and about 0.1 to about 1% by weight $FeSO_4$ to be effective. Preferred amounts of hydrogen peroxide are about 0.5 to about 5 weight percent, based upon the total mixture being treated. We have found that as low as 5 weight percent hydrogen peroxide preferentially removes in excess of 70 percent of the polynuclear aromatic hydrocarbon compounds having 4 to 6 rings. The amount of hydrogen peroxide may also be expressed as about 10 mg to about 0.5 gram per gram of solids, such as soil in a slurry, to be treated. The solid/liquid contacting may be best achieved by suspending the solids in a liquid slurry. We have found that the chemical treatment portion of the process functions well at comparatively high solids concentrations of about 10 to about 90 weight percent solids, based upon the total slurry. It is preferred that agitation of the slurry be maintained for about 1 to about 12 hours following completion of hydrogen peroxide addition. The pH of the slurry being treated should be acidic and preferably a pH of about 3.5 to about 5.5 is suitable.

The chemical treatment portion of the chemical/biological treatment process of this invention is carried out at about 10° C. to about 100° C. We have found a significant decrease in desired oxidation of polynuclear aromatic hydrocarbon compounds at both lower and higher temperatures. We prefer to carry out the chemical treatment portion of the process of this invention at temperatures about 20° C. to about 40° C. In preferred embodiments, due to the exothermic nature of the chemical reactions, the temperature is maintained by slow addition of hydrogen peroxide to the slurry solution containing at least sufficient ferrous ion to react with all of the hydrogen peroxide to be added. The ferrous ion may be provided in an aqueous solution by hydrated $FeSO_4$ or any other iron salt or source which will provide the ferrous ion in the liquid solution. We have found suitable rates of addition of hydrogen peroxide to the liquid solution to maintain desired temperatures are between about 1 milligram to about 300 milligrams hydrogen peroxide per hour per gram of contaminated solid material, dependent upon the material being treated, and preferably about 1 to about 100 milligrams hydrogen peroxide per hour per gram contaminated solid material.

The chemical treatment portion of the process of this invention produces primarily carbon dioxide and water, which are environmentally acceptable, and, to a much lesser extent, partially oxidized products of polynuclear aromatic hydrocarbon compounds, such as hydroxylated or epoxidated compounds, which are much more susceptible to bioremediation than the original polynuclear aromatic hydrocarbons, particularly those containing 4 to 6 rings. In work we have completed, a complex 5-ring compound, benzo(a)pyrene, was labeled with radioactive carbon and our tests showed that up to about 40% of the labeled carbon was collected as $CO_2$ following a single chemical treatment in accordance with the present invention. This represents total oxidation of a substantial portion of the biorecalcitrant material.

The biodigesting portion of the process of this invention may be carried out in any manner known to the art using known techniques for aerobic and/or anaerobic biodigestion of polynuclear aromatic hydrocarbon compounds and other contaminants that may be present in connection with the contaminated solid materials. Recycling of digester effluent solids via the integrated chemical/biological treatment of this invention is especially advantageous. We have found that digestion times of about 3 to about 5 weeks in an in situ mode and about 5 to 10 days in a well-mixed slurry mode will provide maximum polynuclear aromatic hydrocarbon removal when using microorganisms capable of biodigestion of these materials.

In accordance with one embodiment of the process of this invention, in the chemical treatment portion of the integrated process of this invention, a lower alcohol, such as methanol or ethanol or mixtures thereof, is added to the liquid solution. Such addition of a lower alcohol is particularly preferred where large numbers of weathered 4- to 6-ring polynuclear aromatic hydrocarbons are present. Suitable amounts of alcohol are about 0.1 to about 80 volume percent, based on the total slurry and preferably about 1 to about 10 volume percent. The alcohol is miscible in water of the slurry and is not harmful to the later biodigestion process. The presence of alcohol in the slurry results in unexpectedly high and frequently complete oxidation of the polynuclear aromatic hydrocarbons, particularly those with 4 to 6 carbon atoms. This result is unexpected to us because it would be expected that addition of any organic material would quench the activity of the hydrogen peroxide upon the polynuclear aromatic hydrocarbons. For example, we have found inhibition of complete oxidation of benzo(a)pyrene in an amount of about 70 percent inhibition when 10 weight/volume percent glucose or cellulose or lignin is added to the slurry in a similar manner.

In still another embodiment of this invention, polynuclear aromatic hydrocarbon contaminated solids may be treated in-situ by the integrated chemical/biological treatment process. For example, contaminated soil may be sprayed with the solution of ferrous ion and hydrogen peroxide with or without a lower alcohol in the solution for a similar chemical treatment portion of the process as described above. For improved liquid-solid contact to promote desired oxidation of the contaminated solids, it may be desirable to plow or otherwise increase the solid surface area and to agitate the solids. In-situ biodegradation may be carried out in conjunction with the chemical treatment portion of the process by any biodigesting means known to the art and suitable for biodigestion of the contaminants then present. In in-situ biodegradation, site derived microorganisms are preferably used in the digestion process.

In accordance with one embodiment of this invention in which biodegradation is carried out in-situ, a polynuclear aromatic hydrocarbon-degrading consortium suitable for use in accordance with the process of this invention is generated by eluting from the site soil cells in a basic mineral salt media (BSM) comprising, in g/l, 4.26 $NaSO_4$, 6.26 $KH_2PO_4$, 8.00 $Na_2HPO_4$, 4.00 $NH_4Cl$, 0.4 $MgCl_2$, 0.002 $CaCl_2$, and 0.002 $FeCl_3$. A small crystal of various polynuclear aromatic hydrocarbons or a site specific extract of polynuclear aromatic hydrocarbons is added to the BSM as a carbon and energy source. The cells are harvested weekly, starting with 1.2 liters of BSM, centrifuged at 10,000 rpm for 10 minutes. The supernate is discarded and the resulting pellets are resuspended in 100 ml of BSM. A differential centrifugation at 2,000 rpm for 2 minutes is performed to remove the crystals of the polynuclear aromatic hydrocarbons. The pellet is discarded and the supernate is retained as an inoculum. The optical density of the inoculum is adjusted to >750 kletts by diluting with BSM. A klett is an arbitrary unit of optical density produced by a Klett spectrophotometer. 2 ml of the inoculum are resuspended in 1.2 l of BSM to which 1% ethanol extract of polynuclear aromatic hydrocarbons is added.

In accordance with yet another embodiment of this invention where the organopollutants are disposed in a sterile matrix, that is, where the integrated chemical/biological process of this invention is carried out other than in-situ, a suitable consortium of polynuclear aromatic hydrocarbon-degrading microorganisms can be derived from a contaminate-specific enrichment consortium. This enrichment consortium is generated in a similar manner as previously described. A suitable source of cells would be natural soils or sediments that have been exposed to a similar contaminate. After eluting cells from this soil or sludge, the contaminates from the sterile matrix can be slowly added to the enrichment culture with increasing concentration. With time, a consortium of cells will be developed which are specific for the degradation of the contaminate.

In accordance with one embodiment of this invention for in situ treatment, the spent liquid of the chemical treatment portion of the process of this invention is separated and injected into the peripheral region of an underground contaminated plume, a localized concentration of contamination, to control its migration and to provide similar chemical treatment to the underground plume for enhanced in-situ biodegradation.

The following examples of treatment of polynuclear aromatic hydrocarbons and polychlorinated hydrocarbons in accordance with the integrated chemical/biological process of this invention are set forth in considerable detail as to conditions and materials and should not be considered as limiting the invention in any way. Polynuclear aromatic hydrocarbon compounds treated in accordance with the examples set forth hereinbelow were 2- to 6-ring compounds and mixtures thereof. In particular, 4- to 6-ring polynuclear aromatic hydrocarbon compounds treated in accordance with the examples set forth hereinbelow include fluoranthene, pyrene, benz(a)anthracene, chrysene, benzo(b)fluoranthene, benzo(k)fluoranthene, benzo(a)pyrene, indeno(1,2,3-cd)pyrene, dibenzo(a,h)anthracene, and benzo(g,h,i)perylene. 2- to 3-ring polynuclear aromatic hydrocarbon compounds treated in accordance with the examples set forth hereinbelow include naphthalene, acenaphthene, fluorene, phenanthrene, and anthracene.

EXAMPLE I

Soil which was dominated by 4- to 6-ring polynuclear aromatic hydrocarbons, over 98 percent 4- to 6-ring compounds, was dried and mixed to assure homogeneity and measured into 20 gram aliquots. This soil had an original polynuclear aromatic hydrocarbon compounds content of about 890 ppm. Triplicate flasks were established, each with 20 grams of dry soil, for four digestion periods at two hydrogen peroxide treatment levels. For 1 percent $H_2O_2$ treatment, 6.7 ml of 30% $H_2O_2$ was added over a period of 4 hours to 193.3 ml of 10 mM $FeSO_4 \cdot 7H_2O$ solution containing the soil as a slurry and 5% $H_2O_2$ treatment was effected by adding 33.3 ml 30% $H_2O_2$ over a period of 4 hours to 166.7 ml of the $FeSO_4$ solution containing the soil as a slurry. The slurries were maintained overnight on a gyratory shaker at 100 rpm following which the contents from each of the flasks was centrifuged to separate the soil solids from the liquid components. The solids were resuspended in BSM growth medium and each flask inoculated with polynuclear aromatic hydrocarbon degrading bacteria, a mixed aerobic culture enriched from town gas soil and maintained on mixed polynuclear aromatic hydrocarbon extracts from polynuclear aromatic hydrocarbon contaminated soil, and maintained at 30° C. and the flasks taken at sampling times of 0, 1, 3, and 5 weeks. The solids were separated from the slurry by centrifugation, allowed to dry, and Soxhlet extracted according to U.S. EPA SW846 method 3540 using a 1:1 mixture of acetone and hexane as the extraction solution. Extracts were analyzed by U.S. EPA SW846 method 8270 using a GC/MS fitted with an ion trap detector. The data was adjusted for moisture and reported on a dry basis. The results of the 1% and 5% hydrogen peroxide treatments were substantially the same at all time periods and the results after 3 weeks digestion were substantially the same reduction in total polynuclear aromatic compounds as after 5 weeks. Thus the lower hydrogen peroxide treatment level and the shorter digestion time resulted in maximum total polynuclear aromatic hydrocarbon compound removal for the single cycle treatment. With the starting level of total polynuclear aromatic hydrocarbons at about 890 ppm, 26% reduction was observed with the hydrogen peroxide treatment alone and 60% reduction was observed with the hydrogen peroxide treatment followed by biodigestion for 3 weeks. Subsequent cycles of chemical and biological treatment should reduce the polynuclear aromatic hydrocarbon levels even further.

EXAMPLE II

Soil that originally contained about 35,000 to 40,000 ppm total polynuclear aromatic hydrocarbon compounds had been subjected to a variety of amendments including inoculation with polynuclear aromatic hydrocarbon-degrading bacteria, treatment with bioemulsifier, and addition of nutrients to reduce the total polynuclear aromatic hydrocarbon components to 8,000 ppm, primarily polynuclear aromatic hydrocarbon compound having 4 to 6 rings. This treated soil which contained recalcitrant polynuclear aromatic hydrocarbon compounds was dried and mixed to assure homogeneity and divided into 20 gram aliquots. A 3×4 factorial design was set up; one with no hydrogen peroxide treatment and two hydrogen peroxide treatment levels, 1% and 5% volume $H_2O_2$ per volume slurry, by four samplings of 0, 1, 2, and 3 weeks digestion. Triplicate flasks were established, each with 20 grams of dry soil, resulting in 36 flasks. Treatments not amended with hydrogen peroxide had 200 ml of Basal Salts Medium added. The remainder of the flasks had the indicated amount of 10 mM $FeSO_4 \cdot 7H_2O$ solution added prior to addition of $H_2O_2$. For the 1 percent $H_2O_2$ treatment, 6.7 ml of 30% $H_2O_2$ was added over a period of 4 hours to 193.3 ml of 10 mM $FeSO_4 \cdot 7H_2O$ solution containing the soil as a slurry resulting in 1% $H_2O_2$ on a volume basis. The 5% $H_2O_2$ treatment was conducted in a similar fashion with 33.3 ml of 30% $H_2O_2$ added over a period of 4 hours to 166.7 ml of the $FeSO_4$ solution containing the soil as a slurry. The slurries were maintained overnight on a gyratory shaker at 100 rpm. The next day contents from each of the flasks was centrifuged to separate the soil solids from the liquid components. The solids were resuspended in BSM growth medium. Each flask was inoculated with polynuclear aromatic hydrocarbon degrading bacteria and maintained at 30° C. and flasks taken at sampling times of 0, 1, 3, and 5 weeks. Solids were separated from the slurry by centrifugation, allowed to dry, and Soxhlet extracted according to U.S. EPA SW846 method 3540 using a 1:1 mixture of acetone and hexane as the extraction solvent. Extracts were analyzed by U.S. EPA SW846 method 8270 using a GC/MS instrument fitted with an ion-trap detector. All data were adjusted for moisture and expressed on a dry basis. The total polynuclear aromatic hydrocarbons remaining following one sequence of chemical and biological treatment are shown in Table II expressed as ppm.

TABLE II

| Percent $H_2O_2$ | Digestion period in weeks | | | |
| --- | --- | --- | --- | --- |
| | 0 | 1 | 3 | 5 |
| 0 | 8417 | 8387 | 6423 | 6012 |
| 1 | 8417 | 8641 | 3903 | 3447 |
| 5 | 8417 | 4697 | 2502 | 2881 |

The table clearly shows reduction in total polynuclear aromatic hydrocarbon compounds, primarily 4- to 6-ring polynuclear hydrocarbon compounds, using the integrated chemical/biological treatment according to this invention.

After the five week digestion period for which data is shown in Table II, the material from the digesters was pooled and again subjected to the above described chemical treatment with 5% $H_2O_2$ which reduced the primarily 4- to 6-ring polynuclear aromatic hydrocarbon content remaining after biodigestion to 827 ppm, providing a total polynuclear aromatic hydrocarbon compound reduction of 98 percent.

EXAMPLE III

In similar fashion, actual soil contaminated with 250 ppm total polynuclear aromatic hydrocarbon compounds of which 52% were 2–3 ring hydrocarbon compounds and 48% were 4–6 ring hydrocarbon compounds was slurried in 20 mM FeSO$_4$ forming a 20% solids slurry at pH of 4.5 and room temperature. Hydrogen peroxide was added over a period of 16 hours in a total amount of 10 weight percent and the solids analyzed as described by GC/MS and the total polynuclear aromatic hydrocarbon compounds were found to be 152 ppm with 72 ppm being 2–3 ring compounds and 80 ppm being 4–6 ring compounds. A further removal of polynuclear aromatic hydrocarbon compounds was performed in the same manner except 5% by volume methanol was added to the initial slurry and resulted in the final total polynuclear aromatic hydrocarbon compound content of less than 95 ppm with 55 ppm being 2–3 ring compounds and 40 ppm being 4–6 ring compounds. present. This material is readily biodegradable.

EXAMPLE IV

Figure 2:
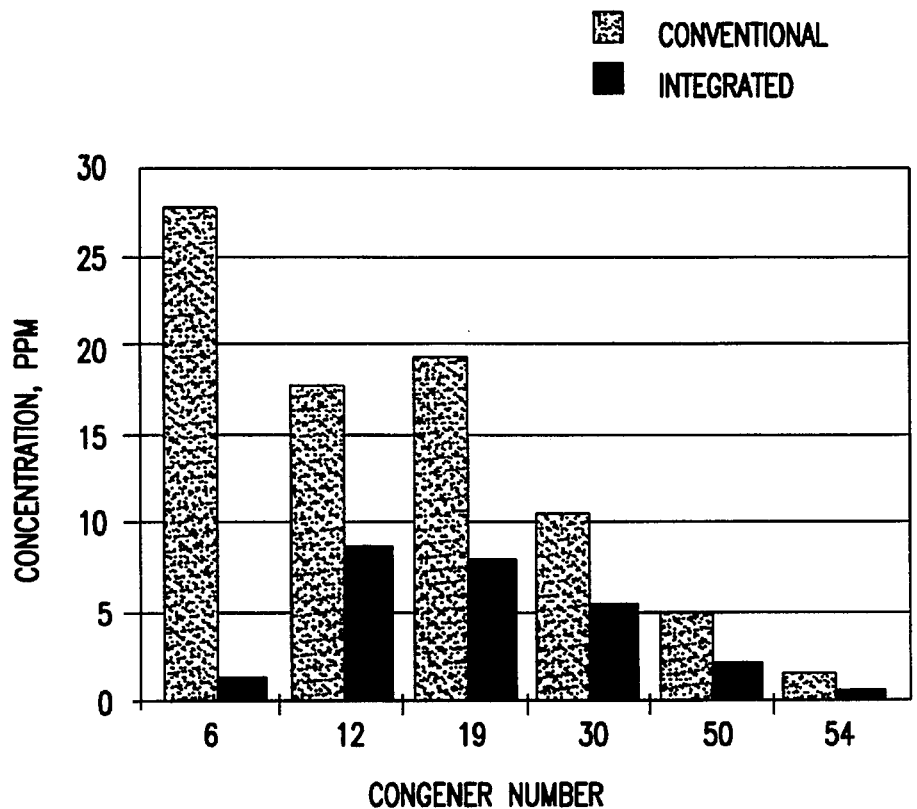
FIG. 2 is a graphic illustration showing a comparison of soil samples treated by conventional biological treatment versus treatment in accordance with the integrated chemical/biological treatment process of this invention.

Sediments containing approximately 250 ppm total PCBs were treated with an integrated treatment in a 10% sediment slurry which consisted of a biological treatment (1 week), followed by a chemical treatment (1 week), and followed by another biological treatment (1 week). FIG. 2 shows a comparison of the results of degradation of PCBs in soil by conventional means, that is, biological treatment alone, versus treatment in accordance with the integrated chemical/biological process of this invention. FIG. 2 shows a comparison of the remaining PCBs in a sediment after three weeks of conventional biological treatment and after three weeks of integrated chemical/biological treatment.

In accordance with the procedure utilized for biological treatment alone of the contaminated soil, the PCB degrading cultures were obtained from various sources for their ability to grow in biphenyl broth and biphenyl plates. A procedure for preparing biphenyl broth and biphenyl plates is described in Bedard, D. L. et al., *Applied and Environmental Microbiology*, 51(4), pp. 761–8. The biphenyl was the sole source of carbon. Growth in the broth was based on visual observation of turbidity. Five cultures were able to grow in the biphenyl broth and, when transferred to the biphenyl plate, grew on the plate. The five cultures were three pure cultures identified as Pi434, H430, and H1103 and two mixed cultures isolated from PCB-1 soils. The cultures were pre-grown, mixed together and added to a 10% soil slurry. The soil was subsequently examined for the removal of PCBs.

In the treatment of the contaminated soil in accordance with the integrated chemical/biological process of this invention, the biological degradation was carried out as discussed above. However, prior to initiation of the biological treatment, chemical treatment was carried out as previously described with the exception that 10% hydrogen peroxide was utilized. Due to the higher concentration of hydrogen peroxide, the chemical oxidation was allowed to proceed for 1 week before biological degradation was initiated. No lower alcohols were added.

EXAMPLE V

A study to evaluate the effects of the combination of chemical and biological treatment of PCBs in accordance with the process of this invention on the rate and extent of degradation of various pure PCB congeners was carried out as follows.

All chemicals were reagent-grade and included toluene, hydrogen peroxide, and ferrous sulfate; HPCL-grade 2-chlorobiphenyl (2-CB), 2,2',4,4'-tetrachlorobiphenyl (2,2', 4,4'-TCB); 2-Chlorobiphenyl-UL-$^{14}$C (4.9 mCi/mmol, purity >98%) and 2,2',4,4'-tetrachlorobiphenyl-UL-$^{14}$C (10.6 mCi/mmol, purity <98%).

The organisms used in this experiment were *Alcaligenes eutrophus*, strain H850 (NRRL 15940) and *Pseudomonas sp.*, strain LB400 (NRRL 18064), obtained from General Electric Co., Schenectady, N.Y. Cells were harvested by centrifugation near the midpoint of log phase of growth, washed twice with 0.05M sodium phosphate buffer (pH 7), and resuspended in phosphate-buffered mineral salts medium to obtain a cell density of approximately $1 \times 10^8$ cells/ml. After mixing in equal proportions, cells were added to the experimental systems for a final cell density of $2.5 \times 10^6$ cells/ml.

Figure 3:
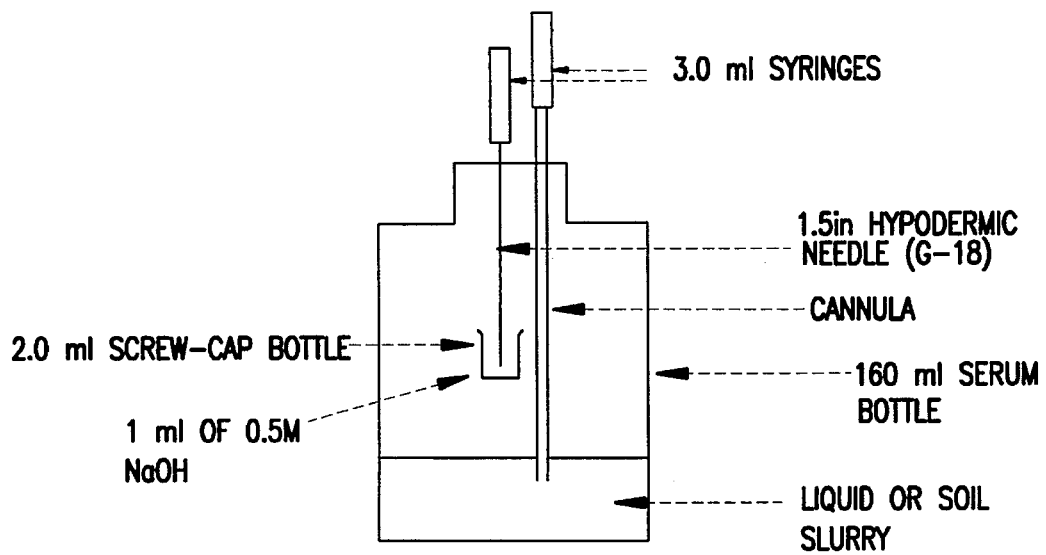
FIG. 3 is a schematic diagram of a 160 ml serum bottle apparatus utilized in experiments showing the operability of the process of this invention as discussed hereinbelow.

To measure the rate of chemical transformation of PCBs by Fenton's reagent, unlabeled (0.25 mg) and labeled (100, 000 dpm) congeners, dissolved in toluene, were added to the bottom of a 160-ml serum bottle apparatus, as shown in FIG. 3. The toluene was allowed to evaporate, and acetate buffer and ferrous sulfate solutions were added. Acetate buffer was used to achieve a pH of 4.0. The serum bottles were crimp-sealed and 1 ml of 0.5M NaOH was added to one 2 ml screw cap vial inserted in the bottle and a second vial received 1 ml of n-butanol. These vials allow for trapping of CO$_2$ and volatile organics, respectively. Aliquots of hydrogen peroxide stock solution (30%) were injected into the bottles for a final concentration of 1%. The final volume in each bottle was 25 ml. The bottles were shaken on a rotary shaker (120 rpm) throughout the experiment at approximately 22° C. Periodically, the NaOH or n-butanol from the traps and 1.5 ml of liquid from the bottle were removed, and the NaOH or n-butanol was replaced. Samples from the liquid phase of the reaction mixture were passed through sterile nylon syringe filters (0.22-μm pore size) to remove solid particles. The NaOH, n-butanol, and filtered liquid (1 ml) were mixed with 4 ml of Ultima Gold scintillation fluid in 7-ml scintillation vials, and the radioactivity was determined with a liquid scintillation analyzer. To assess the radioactivity associated with biomass and inorganic particles, the filters were dissolved in toluene, and the radioactivity was counted.

After completion of the chemical reaction, the pH in each of the experimental systems was adjusted to 8.0 with NaOH and microbial cells, along with phosphate-buffered mineral salts medium, were added to the bottles for a final volume of 40 ml. The pH was measured daily and adjusted to 8.0 thereafter. The evolution of CO$_2$ and organics, along with the dynamics of the specific radioactivity associated with solids and the liquid phase, were monitored. After the experiments were terminated, residues attached to the glass walls of the experimental vessels were extracted by adding 25 ml of toluene, shaking bottles for 24 hours and counting toluene 09 March 1995.

Experiments on the biodegradation of PCBs without chemical pretreatment were carried out in phosphate buffer and maintained at pH 8.0 throughout the experiments.

Duplicate bottles were used in all studies. Data were analyzed statistically at the 95% confidence level.

Experiments were conducted on the volatilization and mineralization of two test PCB congeners, and a mass-balance was generated. The total recovery of radioactivity added was greater than 84% in all experiments as shown in Table III.

TABLE III

Final Distribution of Radioactivity Between Different Parts of Experimental System, % of Initial Radioactivity Added

| PCBs | $CO_2$ | Volatile | Liquid | Biomass | Glass | Total |
|---|---|---|---|---|---|---|
| Control (no treatment) | | | | | | |
| 2-CB | 1.0 | 18.5 | 0.9 | — | 70.2 | 90.6 |
| TCB | 0.1 | 5.2 | 0.1 | — | 82.5 | 87.9 |
| Biological Treatment | | | | | | |
| 2-CB | 45.0 | 8.7 | 3.4 | 15.3 | 22.9 | 96.4 |
| TCB | 8.5 | 1.5 | 2.8 | 7.1 | 75.1 | 95.0 |
| Chemical/Biological Treatment | | | | | | |
| 2-CB | 37.5 | 1.8 | 3.5 | 25.4 | 22.6 | 90.8 |
| TCB | 51.2 | 0.6 | 3.3 | 22.1 | 20.2 | 84.8 |

In the sterile system, sorption to the glass walls was the main factor affecting removal of both PCB congeners. In addition, nearly 19% of 2-CB was removed from the system by volatilization, compared to only 5% for 2,2',4,4'-TCB. Only trace amounts of both PCB congeners were found in the liquid phase at the end of the experiment.

In 2-CB systems amended with microbial cultures, microbial degradation was the major factor affecting overall removal. For 2-CB, 45% of initially added compound was recovered in the form of $CO_2$, while only 8 5% of 2,2',4, 4'-TCB was mineralized. A portion of the initially added congeners was partially metabolized causing an increase in radioactivity in the liquid phase and its association with the cell biomass. Microbial degradation appeared to compete with volatilization, and in controls with no microorganisms, volatilization decreased more than two and three times in the bottles with 2-CB and 2,2',4,4'-TCB, respectively Biodegradation of 2-CB also affected the amount of compound sorbed to the glass walls, with a 47.3% reduction, while the amount of 2,2',4,4'-TCB sorbed to the glass walls in the presence of microbial cultures was reduced only 7.4% compared to sterile controls.

The application of chemical pretreatment by Fenton's reagent affected consequent biodegradation of mono- and tetrachlorinated PCB congeners differently (Table III). While a slight decrease was observed for the extent of 2-CB mineralization, a 6-fold increase was observed for 2,2',4,4'-TCB. Chemical oxidation also decreased sorption of 2,2',4, 4'-TCB to the glass walls almost 4-fold, when compared to the varieties with biological treatment only. At the same time, application of Fenton's reagent did not significantly affect the extent of accumulation of water soluble compounds in the liquid phase of the experimental system. On the contrary, at the end of the experiment, more than 10% of the initially added radioactivity was found in the liquid phase of the bottles chemically treated but not inoculated with microorganisms. HPLC analyses of the liquid phase of the experimental systems treated with Fenton's reagent showed no detectable amounts of the parent compounds tested during the course of the experiments.

Biodegradation kinetics in bottles with microorganisms and no chemical treatment approached first-order in the case of 2-CB, resulting in the production of nearly 90% of all [14-C] $CO_2$ in the first 125 hours of the experiment. Correlation analyses showed that kinetics in the case of 2,2',4, 4'-TCB were also close to first-order with a lag-phase of approximately 25 hours following the addition of microbial cultures. Application of Fenton's reagent drastically changed the maximum rate of 2,2',4,4'-TCB degradation from 0.14 µg/hour in the biological treatment alone to 0.92 µg/hour in the chemical-biological treatment. Chemical pretreatment of 2-CB resulted in a 15-fold decrease in the highest rate of 2-CB biodegradation.

Figure 4A:
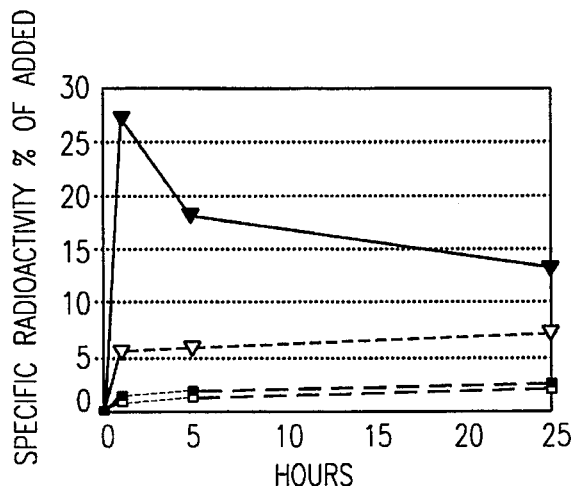
FIG. 4 is a graphic illustration showing the results of treatment of PCBs in accordance with the process of this invention.
Figure 4B:
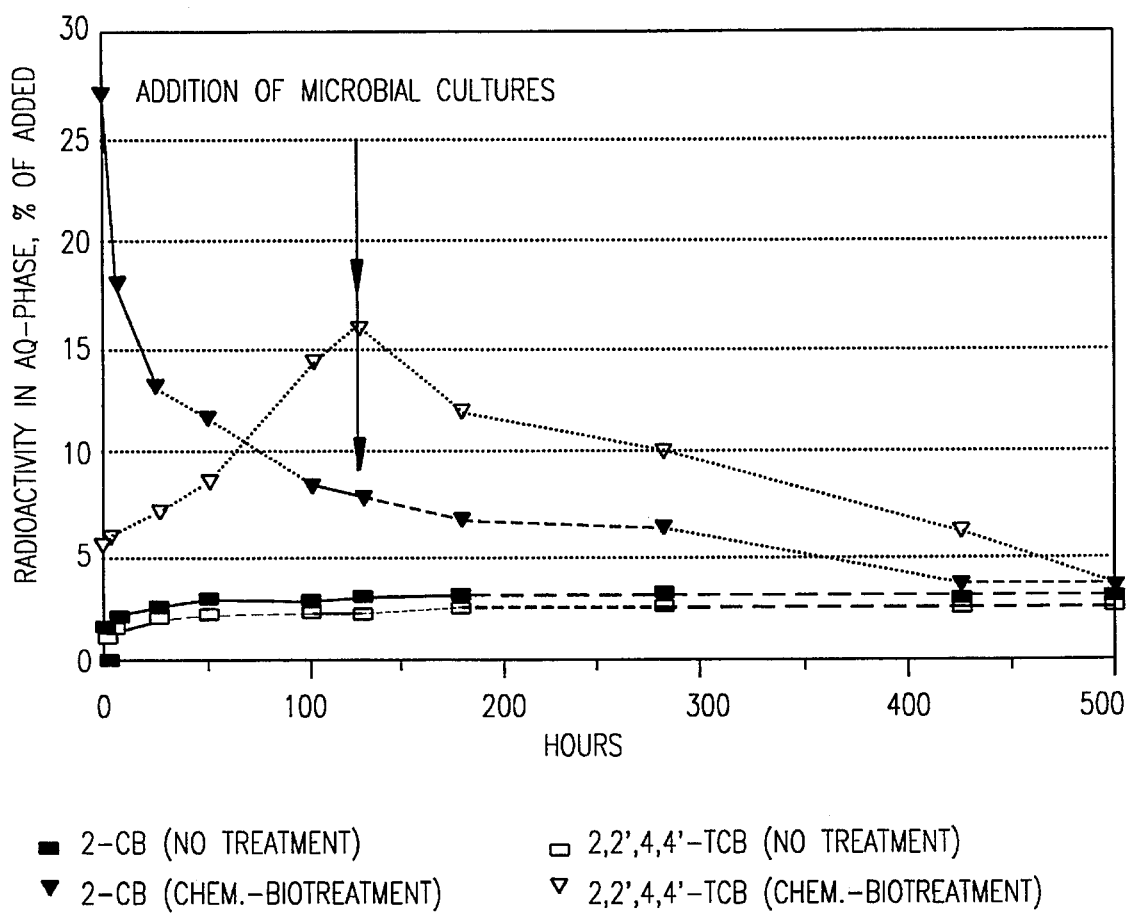

The analysis of radioactivity in the liquid phase of the experimental system amended with [14-C]2-CB showed an increase from 5% to nearly 30% of initial radioactivity added within the first hour after initiation of chemical treatment (insert in FIG. 4), followed by a decrease to near the initial level at the end of the experiment (FIG. 4). The shape of curve depicting the dynamics of radioactivity in the system amended with [14-C]2,2',4,4'-TCB was also biphasic, although in this case the beginning of the second phase was clearly associated with the addition of microbial cultures. During the first phase (chemical oxidation), the amount of radioactivity in the liquid phase increased to 16% of initial radioactivity added, and after inoculation, decreased to 5% (FIG. 4).

Oxidation by Fenton's reagent followed by application of *Alcaligenes eutrophus*, strain H850 (NRRL 15940) and Pseudomonas, strain LB 400 (NRRL 18064) allowed greater than 50% removal of tetrachlorinated PCB congener. This result does not exceed the mineralization values for 2,2',4, 4'-TCB previously reported for microbial or chemical methods used separately. However, it should be noted that in the studies on biological degradation of PCBs, the limitations of mass-transfer of chemicals practically insoluble in water were avoided by direct addition of concentrated solutions of PCBs in acetone to the cell suspensions. In chemical degradation experiments, these limitations were overcome by either the addition of chemicals dissolved in non-aqueous phase liquids or below their solubility limits. In our study, substantial amounts of PCBs and their intermediates (up to 75% of added) were recovered from the glass walls at the end of the experiments. Chemical and enzymatic reactions in the presence of sorbed and/or undissolved chemical are heterogenous and, thus, environmentally realistic.

Application of Fenton's reagent dramatically increased the effectiveness of biodegradation of a highly chlorinated PCB congener. In contrast, the extent of the combined chemical/biological degradation of a monochlorinated congener was slightly lower compared to that achieved by biological means alone. The lag-phase observed for biodegradation of partially oxidized products resulting from chemical treatment of PCB congeners indicates the possibility of the direct effect of these products on microbiological activity. HPLC analyses of the liquid phase confirmed that all radioactivity exists in the form of unidentified water soluble compounds. A previously described intermediate in the chemical degradation pathway of 2-chlorobiphenyl is 5-hydroxy-2-chlorobiphenyl. Representatives of mono-hydroxybiphenyls have been found to act as antibiotic agents, and may inhibit microbial degradation. Possible toxic intermediates generated by chemical oxidation of polychlorinated biphenyls include also polychlorinated dibenzofurans (PCDF).

The amount of 2,2',4,4'-TCB mineralized during the biological stage of combined chemical/biological treatment was nearly 40%. This was three times greater than the decrease of radioactivity in the aqueous phase of the experimental system after the application of microbial cultures. This suggests that microorganisms may have degraded the portion of the parent compound which had been chemically altered, but not desorbed. Marked enhancement of the rate and/or extent of biphenyl's biodegradation without its substantial desorption has been observed in soils and aquifer solids with the application of two nonionic surfactants at low concentrations. Although the surfactant-based and oxidant-based mechanisms of chemical alteration are different, they may both lead to the direct microbial consumption of some organic compounds adhered to the solid surfaces.

Thus, the evaluation of experimental data suggests two possible means of microbial utilization of tetrachlorinated PCB congeners altered by chemical oxidation: (a) consumption of the partially oxidized chemical dissolved in the aqueous phase, and (b) direct microbial attack on the altered compound, still adhered to the solid surface. In addition, the data clearly show that chemical pretreatment of PCBs increases the availability of PCBs for microbial degradation and, thus, provides a synergistic effect in the treatment of PCBs utilizing the integrated chemical/biological treatment process of this invention which is not available or discernible from treatment of PCBs utilizing separate chemical and biological treatment processes.

EXAMPLE VI

In addition to in vitro studies, we have successfully demonstrated the integrated chemical/biological treatment process of this invention in the field, i.e. in situ. Several experimental designs were evaluated. One treatment plot design included four treatment cells with dimensions of 4'×12' each. A different land treatment technology was applied to each of the plots, with one of the plots acting as a control. Another treatment design utilized eight treatment plots, also 4'×12' each. The purpose of this design was to provide repetition in treatment and analysis, and thus reduce random error. A third design included a total of sixteen treatment plots, also 4'×12', four of which were dedicated to one of four land treatment technologies. However, the sixteen plots were loaded in random sequence, thus minimizing errors associated with loading, treatment and analysis.

A liner system was created under each treatment plot to facilitate water management and prevent contamination of the underlying soil. Above the liner was a layer of rock or gravel, then clean sand, followed by 15–20 cm of polynuclear aromatic hydrocarbon contaminated soil. Each of the treatment plots was bounded by boards, thereby making possible weekly or biweekly tilling of the various plots using a garden tractor equipped with a rototiller. Decontamination of the equipment was performed between each treatment plot. A water management system was established to hold water derived from each of the treatment plots and the decontamination zone in an onsite impoundment. Collected water was used for irrigation during the experiment. Meteorological data were collected for ambient temperature, wind speed and direction, and precipitation. Soil samples were collected at the beginning of the experiment and after 1 day, and after 1, 2, 4, 6, 8, and 10 weeks of treatment. Parameters measured included PAHs, nutrient levels, microbial population levels, pH, and moisture.

In one field study, the main conditions evaluated were: Treatment 1—unamended control; Treatment 2—amendment with nutrients, tilling, and irrigation; Treatment 3—amendment with nutrients, tilling, moisture, and Fenton's reagents at the beginning of the study and on a periodic basis by adding hydrogen peroxide directly to the soil during irrigation.

Figure 5:
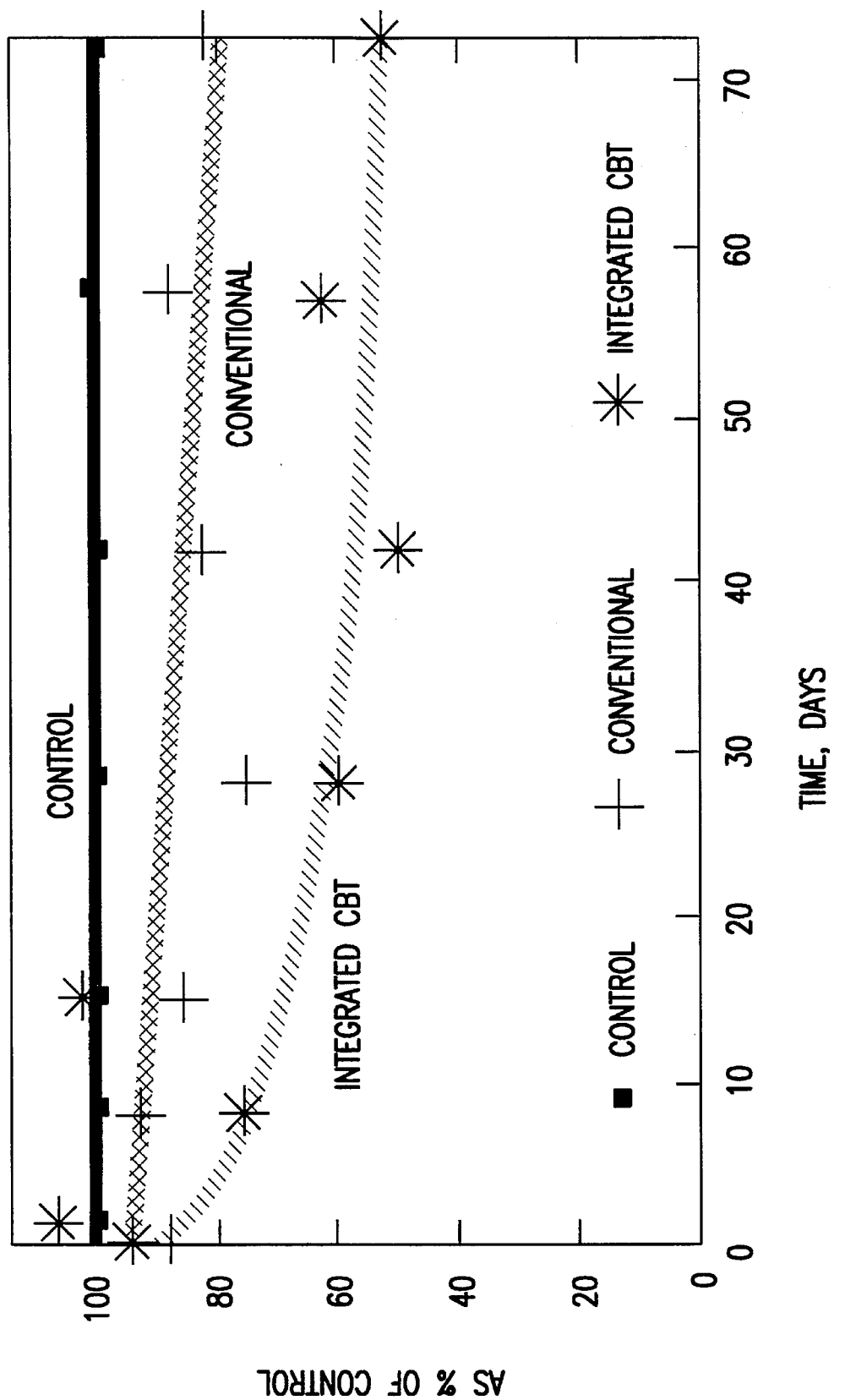
FIG. 5 is a graphic illustration showing the results of field tests of the process of this invention on polynuclear aromatic hydrocarbons.

The primary objective of this field experiment was to compare PAH degradation as a direct consequence of microorganisms, or from chemical treatment using Fenton's reaction as a pretreatment or as a cotreatment in conjunction with biological processes. FIG. 5 shows the results of the field test described hereinabove. In this figure, the residual PAH concentrations in the soil are compared with control plots that did not receive any nutrients, conventional bioremediation plots that received nutrients, and treatment plots treated in accordance with the integrated chemical/biological treatment of this invention. Because the soil naturally contained nutrients, the control plots also exhibited some degradation of PAHs. Thus, FIG. 5 shows the PAH reductions over and above those observed in the control plots. Table IV shows the percent degradation of PAHs in each treatment plot group as total EPA PAHs and carcinogenic EPA PAHs (as defined by the US EPA) after 42 days.

TABLE IV

Total PAH Reduction After 42 Days of Treatment

| Treatment | Explanation | PAH reduction, percent | |
|---|---|---|---|
| | | Total PAHs | Carcinogenic PAHs |
| 1 | Control, not managed | 41 ± 7 | 29 ± 5 |
| 2 | Conventional Bioremediation, addition of N + P at 21 days | 49 ± 6 | 29 ± 3 |
| 3 | Integrated chemical/biological treatment, chemical addition as cotreatment at day 1 and day 29 | 72 ± 6 | 56 ± 4 |

Initial land treatment of 1% chemical treatment on day 0 and additional 1% chemical treatment on day 29 appears to give the best results with higher PAH degradation and at a faster rate of degradation. The integrated treatment reduced PAHs at a higher rate and to a greater extent than the conventional bioremediation. The treatment goals for this soil were met within the first 28 days when using the integrated chemical/biological treatment process of this invention.

Meteorological data collected included ambient temperature (both air and soil), wind speed and direction, precipitation, and relative humidity. Nighttime temperatures below 32° F. were first seen after 31 days of operation, and soil temperatures below 45° F. were observed after 40 days of operation. During the test period the daytime air temperature varied between a high of about 85° F. and a low of about 40° F. and soil temperature varied between a high of about 94° F. and a low of about 42° F.

The results of our studies can be summarized as follows:
1) Bioremediation is effective in removing PAHs from PAH-contaminated soils;
2) The integrated chemical/biological treatment process of this invention improves the rate as well as the extent of PAH removal; and
3) PAH-contaminated soils can be effectively cleaned in a land farming mode using the integrated chemical/biological treatment process of this invention.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

We claim:

1. A process for remediation of contaminated solid materials selected from the group consisting of polynuclear aromatic hydrocarbon contaminated solid materials, polychlorinated hydrocarbon contaminated materials, and mixtures thereof by integrated chemical/biological treatment comprising the steps of:

contacting for chemical treatment said contaminated solid materials with hydrogen peroxide in the presence of ferrous ion in amounts and conditions suitable for chemical oxidation at a temperature of about 10° C. to about 100° C. forming a mixture, oxidizing said contaminated solid materials producing biodegradable hydrocarbon product materials having enhanced biodegradability, and biodigesting under suitable conditions said product materials by at least one of aerobic and anaerobic biodigestion.

2. A process according to claim 1, wherein the total of said hydrogen peroxide is about 0.1 to about 10 weight percent of said mixture.

3. A process according to claim 1, wherein the total of said hydrogen peroxide is about 0.5 to about 5 weight percent of said mixture.

4. A process according to claim 1, wherein said temperature is about 20° C. to about 40° C.

5. A process according to claim 1, wherein said hydrogen peroxide is added at a rate sufficient to maintain said temperature.

6. A process according to claim 5, wherein said hydrogen peroxide is added at a rate of about 1 milligram to about 300 milligrams hydrogen peroxide per hour per gram of said contaminated solid materials.

7. A process according to claim 5, wherein said hydrogen peroxide is added at a rate of about 1 milligram to about 100 milligrams hydrogen peroxide per hour per gram of said contaminated solid materials.

8. A process according to claim 1, wherein said contaminated solid materials comprise at least one of soil and sediment.

9. A process according to claim 1, wherein said contaminated solid materials comprise about 10 to about 90 weight percent of said mixture.

10. A process according to claim 1, wherein said contaminated solid materials comprise an effluent from at least one of aerobic and anaerobic digestion and said product materials are recycled to at least one of aerobic and anaerobic biodigestion.

11. A process according to claim 1, wherein said hydrogen peroxide and said ferrous ion are disposed in a liquid solution comprising a lower alcohol.

12. A process according to claim 11, wherein said lower alcohol is selected from the group consisting of methanol, ethanol and mixtures thereof.

13. A process according to claim 11, wherein said alcohol is present in an amount of about 0.1 to about 80 volume percent, based upon the volume of said mixture.

14. A process according to claim 11, wherein said alcohol is present in an amount of about 1 to about 10 volume percent, based upon the total mixture.

15. A process according to claim 1, wherein a predominate portion of said polynuclear aromatic hydrocarbon comprises 4 to 6 carbon rings.

16. A process according to claim 1, wherein said polynuclear aromatic hydrocarbon comprise predominately 4 to 6 carbon rings, the total of said hydrogen peroxide is about 0.1 to about 10 weight percent of said contaminated solid materials and said mixture, and said hydrogen peroxide is added at a rate sufficient to maintain said temperature.

17. A process according to claim 16, wherein said lower alcohol is present in an amount of about 0.1 to about 80 volume percent based upon the total said solid materials and said mixture.

18. A process according to claim 1, wherein a polynuclear aromatic hydrocarbon-degrading consortium for biodigestion of said product materials is generated by eluting from said polynuclear aromatic hydrocarbon contaminated solid materials cells in an aqueous solution suitable for biological growth;

harvesting said cells, forming a supernate and at least one pellet;

discarding said supernate and suspending said at least one pellet in said basic mineral salt media;

separating said suspended said at least one pellet from said basic mineral salt media, forming an inoculum;

adjusting the optical density of said inoculum to greater than about 750 kletts by diluting with said basic mineral salt media;

resuspending at least a portion of said inoculum in said basic mineral salt media; and adding an ethanol extract of said polynuclear aromatic hydrocarbons to said resuspended inoculum.

19. A process according to claim 1, wherein a polynuclear aromatic hydrocarbon-degrading consortium for biodigestion of said product materials is generated by eluting from said polynuclear aromatic hydrocarbon contaminated solid materials cells and exposing said cells to the conditions of said chemical treatment.

20. A process according to claim 1, wherein a microorganism for biodigesting said product materials comprises a microbial culture selected from the group consisting of *Alcaligenes eutrophus*, strain H850 (NRRL 15940), Pseudomonas, strain LB 400 (NRRL 18064), *Pseudomonas aeruginosa* (ATCC 15522–28, 21472), *Alcaligenes faecalis* (ATCC 8750), *Rhodotorula rubra* (ATCC 16639), *Xanthomonas maltophilia* (ATCC 25596), and mixtures thereof.

21. A process for in-situ remediation of contaminated soil particles selected from the group consisting of polynuclear aromatic hydrocarbon contaminated soil particles, polychlorinated hydrocarbon contaminated soil particles, and mixtures thereof by integrated chemical/biological in-situ treatment comprising the steps of:

contacting for chemical treatment said contaminated soil particles with hydrogen peroxide in the presence of ferrous ion in amounts and under conditions suitable for chemical oxidation at a temperature of about 10° C. to about 100° C., oxidizing said contaminants producing biodegradable hydrocarbon product materials having enhanced biodegradability, and biodigesting under suitable conditions said product materials by at least one of aerobic and anaerobic biodigestion.

22. A process according to claim 21, wherein said hydrogen peroxide and said ferrous ion are disposed in a liquid solution comprising a lower alcohol.

23. A process according to claim 22, wherein said lower alcohol is present in an amount of about 0.1 to about 80 volume percent, based upon said solid materials and said liquid.

24. A process according to claim 21, wherein a polynuclear aromatic hydrocarbon-degrading consortium for biodigestion of said product materials is generated by eluting from said polynuclear aromatic hydrocarbon contaminated soil particles cells in an aqueous solution suitable for biological growth;

harvesting said cells, forming a supernate and at least one pellet;

discarding said supernate and suspending said at least one pellet in said basic mineral salt media;

separating said suspended said at least one pellet from said basic mineral salt media, forming an inoculum;

adjusting the optical density of said inoculum to greater than about 750 kletts by diluting with said basic mineral salt media;

resuspending at least a portion of said inoculum in said basic mineral salt media; and adding an ethanol extract of said polynuclear aromatic hydrocarbons to said resuspended inoculum.

25. A process according to claim 21, wherein a polynuclear aromatic hydrocarbon-degrading consortium for biodigestion of said product materials is generated by eluting from said polynuclear aromatic hydrocarbon contaminated solid materials cells and exposing said cells to the conditions of said chemical treatment.

26. A process for remediation of predominately 4- to 6-carbon ring polynuclear aromatic hydrocarbon compound contaminated solid material by integrated chemical/biological treatment comprising the steps:

contacting for chemical treatment said polynuclear aromatic hydrocarbon contaminated solid material with hydrogen peroxide in the presence of ferrous ion in a liquid solution comprising at least one lower alcohol, in amounts and under conditions suitable for chemical oxidation, the total amount of said hydrogen peroxide being about 0.1 to about 10 weight percent of said contaminated solid material and said liquid solution, at a temperature of about 10° C. to about 100° C., oxidizing said polynuclear aromatic hydrocarbon material producing biodegradable hydrocarbon product materials having enhanced biodegradability and biodigesting under suitable conditions said product materials by at least one of aerobic and anaerobic biodigestion.

27. A process according to claim 26, wherein said lower alcohol is present in an amount of about 0.1 to about 80 volume percent, based upon said solid materials and said liquid.

* * * * *

UNITED STATES PATENT AND TRADEMARK OFFICE
CERTIFICATE OF CORRECTION

PATENT NO. : 5,610,065

DATED : 11 March 1997

INVENTOR(S) : Robert L. KELLEY et al.

It is certified that error appears in the above—identified patent and that said Letters Patent is hereby corrected as shown below:

On cover page, after "[75] Inventors:" delete lines 1-5 in their entirety and in its place insert:

--Robert L. Kelley, Mt. Prospect, Ill.; Andy H. Hill, Glen Ellyn, Ill.; Vipul J. Srivastava, Forest Park, Ill.; W. Kennedy Gauger, Pflugerville, Texas; John J. Kilbane, II, Woodstock, Ill.--

Signed and Sealed this

Seventeenth Day of June, 1997

Attest:

BRUCE LEHMAN

Attesting Officer

Commissioner of Patents and Trademarks